(12) United States Patent
Maeda

(10) Patent No.: US 12,018,083 B2
(45) Date of Patent: Jun. 25, 2024

(54) METHOD FOR SUPPRESSING REGULATORY T CELL INFILTRATION BY CCR4 INHIBITION AND METHOD FOR TREATING CANINE NEOPLASTIC DISEASE

(71) Applicants: NIPPON ZENYAKU KOGYO CO., LTD., Koriyama (JP); Shingo Maeda, Saitama (JP)

(72) Inventor: Shingo Maeda, Saitama (JP)

( * ) Notice: Subject to any disclaimer, the term of this patent is extended or adjusted under 35 U.S.C. 154(b) by 84 days.

(21) Appl. No.: 17/587,648

(22) Filed: Jan. 28, 2022

(65) Prior Publication Data

US 2022/0144958 A1 May 12, 2022

Related U.S. Application Data

(62) Division of application No. 16/613,673, filed as application No. PCT/JP2018/016920 on Apr. 26, 2018, now abandoned.

(30) Foreign Application Priority Data

May 19, 2017 (JP) ................................. 2017-099911

(51) Int. Cl.
*C07K 16/28* (2006.01)
*A61K 31/517* (2006.01)
*A61P 35/00* (2006.01)

(52) U.S. Cl.
CPC ........ *C07K 16/2866* (2013.01); *A61K 31/517* (2013.01); *A61P 35/00* (2018.01)

(58) Field of Classification Search
CPC .... C07K 16/2866; A61P 35/00; A61K 31/517
See application file for complete search history.

(56) References Cited

U.S. PATENT DOCUMENTS

| 2010/0278844 | A1 | 11/2010 | Balkwill et al. |
| 2012/0164161 | A1 | 6/2012 | Hagemann et al. |
| 2015/0104831 | A1 | 4/2015 | Hagemann et al. |
| 2017/0029825 | A1 | 2/2017 | Reilly et al. |
| 2017/0051067 | A1* | 2/2017 | Hagemann ......... C07K 16/2866 |

FOREIGN PATENT DOCUMENTS

| AU | 2013203369 A1 * | 5/2013 | ............. A61K 31/00 |
| CN | 104622874 A | 5/2015 | |
| JP | 2010-539508 A | 12/2010 | |
| JP | 2014-513519 A | 6/2014 | |

OTHER PUBLICATIONS

Ni et al, Depletion of regulatory T cells by targeting CC chemokine receptor type 4 with mogamulizumab, OncoImmunology 4:7, e1011524; Jul. 2015 (Year: 2015).*
Sakaguchi, S.; et al., "Regulatory T Cells and Immune Tolerance", Cell, vol. 133(5), May 30, 2008, pp. 775-787.
Tominaga, M.; et al., "Flow Cytometric Analysis of Peripheral Blood and Tumor-Infiltrating Regulatory T Cells in Dogs with Oral Malignant Melanoma", J. Vet. Diagn. Invest., vol. 22, 2010, pp. 438-441.
Kim, J.H.; et al., "Correlation of Foxp3 positive regulatory T cells with prognostic factors in canine mammary carcinomas", The Veterinary Journal, vol. 193(1), 2012, pp. 222-227.
Carvalho, M.I.; et al., "A Role for T-Lymphocytes in Human Breast Cancer and in Canine Mammary Tumors", BioMed Research International, vol. 2014, Art. ID 130894, (12 pages).
Mucha, J.; et al., "Immunosuppression in Dogs During Mammary Cancer Development", Veterinary Pathology, 2016, vol. 53(6), pp. 1147-1153.
Maeda, S.; et al., "Expression of CC chemokine receptor 4 (CCR4) mRNA in canine atopic skin lesion", Veterinary Immunology and Immunopathology, 2002, vol. 90, pp. 145-154.
Sugiyama, D; et al., "Anti-CCR4 mAb selectively depletes effector-type FoxP3+CD4+ regulatory T cells, evoking antitumor immune responses in humans", Proc Natl Acad Sci, 2013; vol. 110(44), pp. 17945-17950.
Carvalho, MI; et al., "Intratumoral FoxP3 expression is associated with angiogenesis and prognosis in malignant canine mammary tumors", Vet Immunol Immunopathol, 2016; vol. 178, pp. 1-9.
Sugata, K; et al., "HTLV-1 Viral Factor HBZ Induces CCR4 to Promote T-cell Migration and Proliferation", Cancer Res, 2016; vol. 76(17), pp. 5068-5079.
Remer, M; et al., "Mogamulizumab and the treatment of CCR4-positive T-cell lymphomas", Immunotherapy, 2014; vol. 6(11), pp. 1187-1206.
Weide, B; et al., "Increased CCL17 serum levels are associated with improved survival in advanced melanoma", Cancer Immunol Immunother, 2015; vol. 64(9), pp. 1075-1082.
EPO, "The extended European search report", which was issued in connection with corresponding EP application No. 18801563.0, and dated Feb. 2, 2021 (10 pages).
Yokoyama et al., "Discovery of potent CCR4 antagonists: Synthesis and structure-activity relationship study of 2,4-diaminoquinazolines", Bioorganic & Medicinal Chemistry, 2008, vol. 16, pp. 7021-7032.
Office Action for Corresponding Chinese Application No. 201880030440.8, Issued Apr. 25, 2021, 9 Pages.
Al-Haidari et al., "HMG-CoA reductase regulates CCL17-induced colon cancer cell migration via geranylgeranylation and RhoA activation", Biochemical and Biophysical Research Communications, 2014, vol. 446, pp. 68-72.

* cited by examiner

*Primary Examiner* — Mark Halvorson
*Assistant Examiner* — Dennis J Sullivan
(74) *Attorney, Agent, or Firm* — Lucas & Mercanti, LLP

(57) ABSTRACT

Provided are a treatment method and a therapeutic agent for canine tumor. A pharmaceutical composition for treating canine tumor, comprising, as an active ingredient, a compound that inhibits the binding of canine CCL17 and canine CCR4. A method for predicting the efficacy of a compound that inhibits the binding of canine CCL17 and canine CCR4 on the treatment of canine tumor is also provided.

7 Claims, 27 Drawing Sheets

A

Canine PBMC

B

Canine PBMC
+ Anti-CCR4

Fig. 23

Single administration group of Piroxicam: PR 2/14 (14.3%)
SD 9/14 (64.3%)
PD 3/14 (21.4%)

Combined use group with Mogamulizumab: PR 9/13 (69.2%)
SD 4/13 (30.8%)
PD 0/13 (0 %)

METHOD FOR SUPPRESSING REGULATORY T CELL INFILTRATION BY CCR4 INHIBITION AND METHOD FOR TREATING CANINE NEOPLASTIC DISEASE

CROSS-REFERENCE TO RELATED APPLICATIONS

This Application is a Divisional of U.S. patent application Ser. No. 16/613,673 filed Nov. 14, 2019 which in turn is a 371 of PCT/JP2018/016920, filed Apr. 26, 2018, which claims benefit of Japanese Patent Application No. 2017-099911 filed on May 19, 2017, each of which are incorporated herein by reference herein.

TECHNICAL FIELD

The present invention relates to a compound used for the treatment of canine tumor and a method for utilizing the same.

BACKGROUND ART

The number of companion animals affected with neoplastic disease tends to increase year by year. According to a survey by Anicom Insurance, Inc. in 2013, it has been reported that 1 out of 5 male dogs of 12 years or over has developed neoplastic disease, whereas 1 out of 4 female dogs of 12 years or over has developed neoplastic disease, and that the diseased dogs have gone to animal hospitals. Under such circumstances, the control of neoplastic disease is an important issue in the veterinary area.

Regulatory T cells (Treg) are special helper T cells that express a transcriptional factor called Foxp3. Treg suppresses effector T cells or antigen-presenting cells, directly or mediated by inhibitory cytokines. Hence, Treg is important for regulation or settlement of inflammation (see Non Patent Literatures 1 and 2).

In recent years, it has been reported that Treg is associated not only with the control of inflammation, but also with antitumor immunity. If tumor cells are generated in a body, cytotoxic T cells, natural killer cells, or inflammatory cells such as macrophages attack the tumor cells. This reaction is called "antitumor immunity." However, it has been reported that some tumors induce Tregs around them, so as to suppress the aforementioned immune cells and to avoid antitumor immunity (see Non Patent Literatures 2 and 3). However, a mechanism by which Tregs filtrate into the tumor tissues of dogs or cats has been unknown.

CITATION LIST

Non Patent Literature

Non Patent Literature 1: Sakaguchi S. et al., Cell. 2008, May 30; 133(5): 775-87
Non Patent Literature 2: Tominaga M. et al., J. Vet. Diagn. Invest. 2010, 22: 438-441
Non Patent Literature 3: Kim J. H. et al., Vet. J. 2012, July 193(1): 222-7

SUMMARY OF INVENTION

Technical Problem

The present invention provides: a compound that inhibits the binding of CCL17 and CCR4, such as an anti-CCR4 antibody, wherein the compound is used in the treatment of canine tumor; and a method for treating canine tumor, using the same.

Solution to Problem

The present inventors have conducted intensive studies regarding the mechanism of infiltration of regulatory T cells (Treg) into tumor tissues. As a result, the inventors have discovered that, in a certain type of tumor, Tregs that express CCR4 infiltrate into the tumor tissues by the interaction of the CCR4 in the Tregs with CCL17 in the tumor cells. The present inventors have found that infiltration of Tregs into tumor tissues is suppressed by using a compound that inhibits the binding of CCL17 and CCR4, such as an anti-CCR4 antibody, so that the avoidance of antitumor immunity can be suppressed, thereby completing the present invention.

Specifically, the present invention is as follows.

[1] A pharmaceutical composition for treating canine tumor, comprising, as an active ingredient, a compound that inhibits the binding of canine CCL17 and canine CCR4.
[2] The pharmaceutical composition according to the above [1], wherein the compound that inhibits the binding of canine CCL17 and canine CCR4 is an anti-CCR4 antibody.
[3] The pharmaceutical composition according to the above [1], wherein the compound that inhibits the binding of canine CCL17 and canine CCR4 is 2-[1,4'-bipiperidin]-1'-yl-N-cycloheptyl-6,7-dimethoxy-4-quinazolinamine dihydrochloride.
[4] The pharmaceutical composition according to any one of the above [1] to [3], wherein the canine tumor is selected from the group consisting of transitional cell carcinoma, prostate cancer, breast cancer, malignant melanoma, squamous cell carcinoma, and pulmonary adenocarcinoma.
[5] The pharmaceutical composition according to the above [4], wherein the canine tumor is selected from the group consisting of transitional cell carcinoma, prostate cancer, and breast cancer.
[6] A method for treating canine tumor, comprising administering a compound that inhibits the binding of canine CCL17 and canine CCR4 to a dog.
[7] The method according to the above [6], wherein the compound that inhibits the binding of canine CCL17 and canine CCR4 is an anti-CCR4 antibody.
[8] The method according to the above [6], wherein the compound that inhibits the binding of canine CCL17 and canine CCR4 is 2-[1,4'-bipiperidin]-1'-yl-N-cycloheptyl-6,7-dimethoxy-4-quinazolinamine dihydrochloride.
[9] The method according to any one of the above [6] to [8], wherein the canine tumor is selected from the group consisting of transitional cell carcinoma, prostate cancer, breast cancer, malignant melanoma, squamous cell carcinoma, and pulmonary adenocarcinoma.
[10] The method according to the above [9], wherein the canine tumor is selected from the group consisting of transitional cell carcinoma, prostate cancer, and breast cancer.
[11] A method for predicting the efficacy of a compound that inhibits the binding of canine CCL17 and canine CCR4 on the treatment of canine tumor, using the level of CCL17 in a canine biological sample, wherein the compound is predicted to have high efficacy, when the CCL17 level in the biological sample is high.
[12] The method according to the above [11], wherein the canine biological sample is urine.

[13] The method according to the above [11] or [12], wherein the compound that inhibits the binding of canine CCL17 and canine CCR4 is an anti-CCR4 antibody.

[14] The method according to any one of the above [11] to [13], wherein the compound that inhibits the binding of canine CCL17 and canine CCR4 is 2-[1,4'-bipiperidin]-1'-yl-N-cycloheptyl-6,7-dimethoxy-4-quinazolinamine dihydrochloride.

[15] The method according to any one of the above [11] to [14], wherein the canine tumor is selected from the group consisting of transitional cell carcinoma, prostate cancer, breast cancer, malignant melanoma, squamous cell carcinoma, and pulmonary adenocarcinoma.

[16] The method according to the above [15], wherein the canine tumor is selected from the group consisting of transitional cell carcinoma, prostate cancer, and breast cancer.

The present application claims priority from Japanese Patent Application No. 2017-099911; the disclosure of which is hereby incorporated by reference.

Advantageous Effects of Invention

By inhibiting the binding of canine CCL17 that is a chemokine and canine CCR4 that is a receptor for CCL17, infiltration of regulatory T cells (Treg) into tumor tissues is suppressed, so that canine tumor, in which antitumor immunity is avoided by such infiltration of regulatory T cells, can be treated. Examples of a compound inhibiting the binding of canine CCL17 and canine CCR4 may include an anti-CCR4 antibody and C-021 as a CCR4 antagonist.

BRIEF DESCRIPTION OF DRAWINGS

FIG. 23 shows the results obtained by comparing the therapeutic effects of a single administration group of Piroxicam with those of a combined use group with Mogamulizumab according to RECIST.

DESCRIPTION OF EMBODIMENTS

Figure 1:
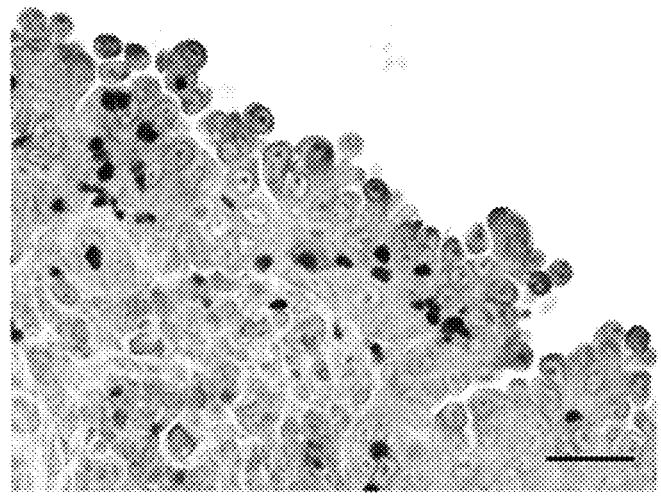
FIG. 1 is an immunohistochemically stained image of Foxp3 showing intratumoral infiltration of Tregs in transitional cell carcinoma.

Hereinafter, the present invention will be described in detail.

The present invention relates to: a method for treating canine tumor, which comprises inhibiting the binding of canine CCL17 that is a chemokine (TARC: Thymus and activation regulated chemokine) and canine CCR4 that is a receptor for CCL17, so as to suppress infiltration of regulatory T cells (Tregs) into tumor tissues; and an agent for treating canine tumor, comprising, as an active ingredient, a compound that inhibits the binding of CCL17 and CCR4, wherein the therapeutic agent is used for the treatment.

In canine tumor cells, the expression of CCL17 is increased. Tregs expressing CCR4 as a receptor for CCL17 infiltrate into tumor tissues, as a result of the interaction of the CCR4 of the Tregs with the CCL17 of the tumor cells. When such Tregs are present around the tumor cells, immune cells that attack the tumor cells are suppressed, and antitumor immunity is avoided.

In the present invention, the interaction of CCL17 expressed in tumor cells with CCR4 expressed in Tregs is suppressed, so that infiltration of Tregs into tumor tissues is suppressed. As a result, the avoidance of antitumor immunity is inhibited, the antitumor immunity is activated, and the tumor cells are attacked by the antitumor immunity, which leads to the treatment of tumor.

The compound that inhibits the binding of CCL17 and CCR4 is not limited, but examples of the compound may include a CCR4 antagonist and a CCL17 antagonist. The term "antagonist" is used herein to mean a substance that binds to a receptor or a ligand and then inhibits the binding of the receptor and the ligand. Examples of the CCR4 antagonist may include an anti-CCR4 antibody, a peptide binding to CCR4, and a low-molecular-weight compound binding to CCR4. Examples of the CCL17 antagonist may include an anti-CCL17 antibody, a peptide binding to CCL17, and a low-molecular-weight compound binding to CCL17. The low-molecular-weight compound binding to CCR4 may be, for example, C-021 (C-021 dihydrochloride; 2-[1,4'-bipiperidin]-1'-yl-N-cycloheptyl-6,7-dimethoxy-4-quinazolinamine dihydrochloride) (CAS 864289-85-0).

Among these, an anti-CCR4 antibody and an anti-CCL17 antibody are preferable, and an anti-CCR4 antibody is particularly preferable. Antibodies reacting against CCL17 or CCR4 derived from mammals other than dogs may also be adequate, and for example, an antibody reacting against human CCR4 may be used. However, antibodies reacting against canine CCL17 or CCR4 are preferably used. In addition, the species as an origin of the antibody used in the present invention is not limited, and antibodies derived from animal species other than dogs, such as, for example, human antibodies, cat antibodies, mouse antibodies, and rat antibodies, may also be used. However, from the viewpoint of avoiding immune responses upon administration thereof to dogs, a canine antibody is preferable. The human antibody may be, for example, Mogamulizumab that is a human anti-CCR4 antibody. Moreover, examples of the antibody used in the present invention may also include: a chimeric antibody having a variable region of an antibody derived from animal species other than dogs and a constant region of a canine antibody; and a reshaped caninized (dog-ized) antibody produced by transplanting the complementarity determining region (CDR) of another animal species-derived antibody into the complementarity determining region of a canine antibody. The antibody of the present invention also includes a functional fragment of an antibody or a modified form thereof. For example, the functional fragment of an antibody is an antibody fragment capable of specifically binding to an antigen. Examples of the functional fragment may include Fab, F(ab')2, Fv, Fab/c having one Fab and complete Fc, and a single chain Fv (scFv) in which the variable regions of H and L chains are connected with one another using a suitable linker.

The antibody of the present invention may be either a monoclonal antibody or a polyclonal antibody, but it is preferably a monoclonal antibody. In addition, the present antibody may also be a recombinant antibody obtained by inserting DNA encoding an antibody into an expression vector, then transforming host cells with the expression vector, and then culturing the host cells. The DNA encoding an antibody is obtained by connecting DNA encoding a heavy chain variable region with DNA encoding a heavy chain constant region, and further connecting a light chain variable region with DNA encoding a light chain constant region, in the form of DNA encoding a heavy chain and DNA encoding a light chain.

According to the method of the present invention, canine tumor can be treated. The tumor as a therapeutic target is a tumor, in which antitumor immunity is avoided as a result of infiltration of Tregs into tumor tissues. Examples of such canine tumor may include transitional cell carcinoma, prostate cancer, breast cancer, malignant melanoma, squamous cell carcinoma, and pulmonary adenocarcinoma. Among these, transitional cell carcinoma, prostate cancer, and breast cancer are preferable.

The dosage form of a formulation comprising the antibody of the present invention is not limited. The formulation comprising the antibody of the present invention can be administered via oral administration, parenteral administration, transmucosal administration (e.g., sublingual or buccal administration), topical administration, transdermal administration, rectal administration, inhalation (e.g., nasal or deep lung inhalation), etc. Examples of the parenteral administration may include intravenous, subcutaneous, and intramuscular injections. The topical or transdermal formulation is used in the form of powders, an emulsion, a suspension, a spray, etc. The amount of the antibody of the present invention necessary for the treatment is different depending on the properties of a disease to be treated, and the age and conditions of a subject dog, and the amount of the present antibody used can be finally determined by a veterinarian in charge. For instance, the antibody may be administered to a subject dog in an amount of 0.05 to 10 mg/kg of body weight, and preferably 0.1 to 2 mg/kg of body weight for a single administration. Moreover, a low-molecular-weight compound such as C-021 may be administered in an amount of 0.01 to 300 mg for a single administration. The predetermined dose may be administered at once, or may also be administered over several divided administrations such as twice, three times, four times, or more times per day, with suitable intervals.

The present invention also includes a pharmaceutical composition comprising, as an active ingredient, a compound that inhibits the binding of CCL17 and CCR4, wherein the pharmaceutical composition is a therapeutic agent for treating canine tumor. The present invention further includes a method for treating canine tumor, comprising administering a compound that inhibits the binding of CCL17 and CCR4 to a dog.

The present invention further includes an agent and a method for treating the tumors of other non-human animals, other than dogs, preferably companion animals such as a cat, a swine, a rabbit, a ferret, or a hamster. When an antibody is used as a therapeutic agent, an antibody reacting against CCL17 or CCR4 derived from each animal species, wherein the antibody is derived from such each animal species, is preferably used.

Since the expression of CCL17 is increased in canine tumor cells, the CCL17 level in a canine biological sample from a dog affected with tumor such as transitional cell carcinoma becomes a high value. The biological sample used herein is urine, blood, serum, plasma, or the like. When canine tumor is treated by administering a compound that inhibits the binding of canine CCL17 and canine CCR4 to dogs, a dog having a high CCL17 level in urine before administration of the compound has a short survival period and poor prognosis, in comparison to a dog having a low CCL17 level in urine before administration of the compound, in the case of analyzing the overall survival period.

Moreover, before the compound that inhibits the binding of canine CCL17 and canine CCR4 is administered to a dog with canine tumor so as to treat the canine tumor, the CCL17 level in urine is measured, and thereafter, the therapeutic effects of the compound are examined. As a result, it is found that the higher the CCL17 level in urine, the higher the therapeutic effects that can be obtained.

Accordingly, by using, as an indicator, the CCL17 level in a biological sample such as urine, the efficacy, namely, the therapeutic effects of the compound that inhibits the binding of canine CCL17 and canine CCR4 on the treatment of tumor can be predicted. For example, when the CCL17 level in urine is 200 pg/mg Cre or more, preferably 300 pg/mg Cre or more, further preferably 500 pg/mg Cre or more, and still further preferably 1000 pg/mg Cre, the efficacy of the compound can be predicted to be high.

The present invention includes a method for predicting the efficacy of a compound that inhibits the binding of canine CCL17 and canine CCR4 on the treatment of canine tumor, using the level of CCL17 in a canine biological sample, wherein the compound is predicted to have high efficacy, when the CCL17 level in the biological sample is high.

The measurement of the CCL17 level can be carried out, for example, by ELISA (Enzyme-Linked ImmunoSorbent Assay) using an anti-CCL17 antibody.

EXAMPLES

The present invention will be specifically described in the following examples. However, these examples are not intended to limit the scope of the present invention.

Figure 2:
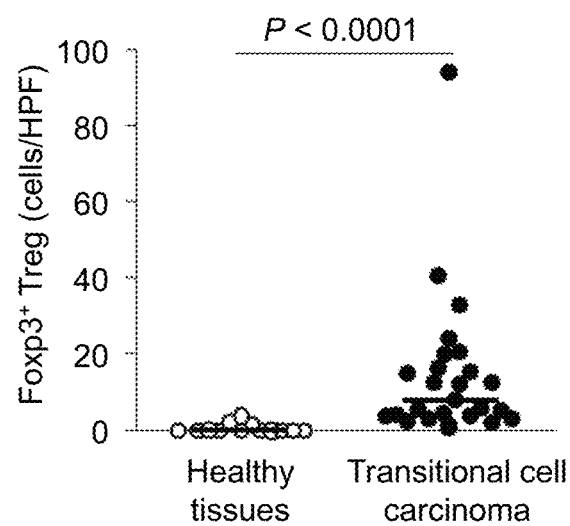
FIG. 2 is a view showing the number of Tregs infiltrating into tumor, per high power field, in transitional cell carcinoma.
Figure 3:
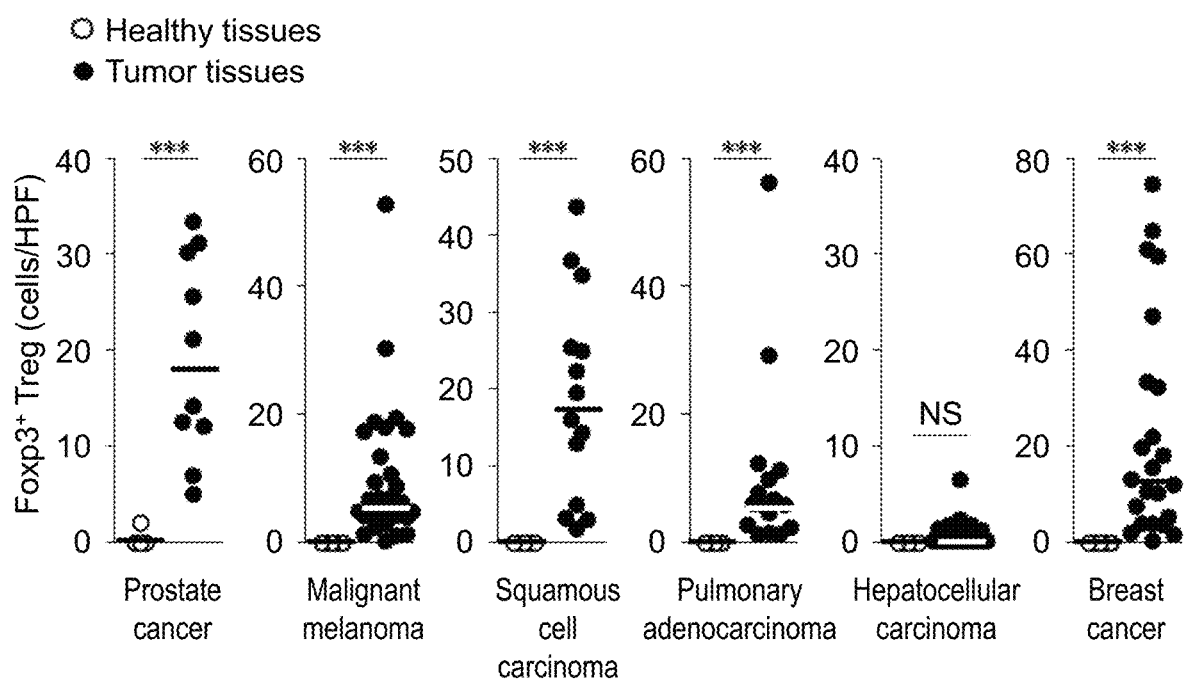
FIG. 3 is a view showing the number of Tregs infiltrating into tumor, per high power field, in various types of tumor tissues.

[Example 1] Analysis Regarding Infiltration of Tregs (Regulatory T Cells) into Various Types of Canine Tumor Tissues Using surgically resected various types of tumor tissues, Foxp3 that is a specific marker of Tregs was subjected to immunohistochemistry to evaluate intratumoral infiltration of Tregs. As a result, infiltration of Tregs was confirmed in the tissues of transitional cell carcinoma, prostate cancer, malignant melanoma, squamous cell carcinoma, pulmonary adenocarcinoma, and breast cancer. FIG. 1 shows an immunohistochemically stained image of Foxp3 in transitional cell carcinoma, wherein the portions seen as black points in the black-and-white photograph are sites in which Foxp3-positive Tregs are present. FIG. 2 shows the number of Foxp3-positive Tregs per high power field (HPF) in transitional cell carcinoma. FIG. 3 shows the number of Foxp3-positive Tregs per high power field (HPF) in various types of tumor tissues. Further, it became clear that a survival period is significantly short in cases where Tregs infiltrate at a high level into tumor tissues.

[Example 2] Identification of Treg Migration Factor

Figure 4:
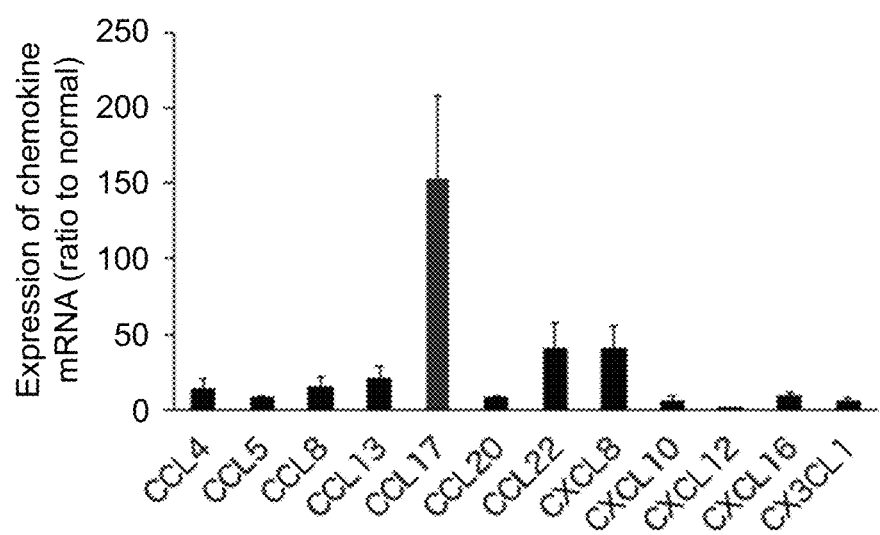
FIG. 4 is a view showing the expression levels of various types of chemokines in canine bladder transitional cell carcinoma tissues.

Total RNA was extracted from each of normal canine bladder and bladder transitional cell carcinoma tissues, and it was then subjected to RNA-Seq using a next-generation sequencer (NextSeq500, Illumina), so that the gene expression was comprehensively analyzed. Among genes whose expression increased in transitional cell carcinoma, molecules associated with cell migration were searched. As a result, the expression of a chemokine called CCL17 was increased to approximately 150 times that in normal tissues (FIG. 4).

[Example 3] CCR4 (CCL17 Receptor) Expression Analysis

Figure 5:
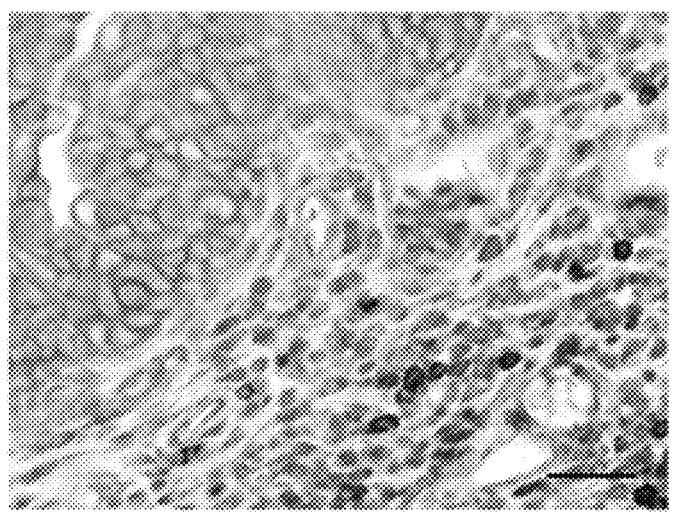
FIG. 5 is a view showing an immunohistochemically stained image showing intratumoral infiltration of CCR4 cells into transitional cell carcinoma.
Figure 6:
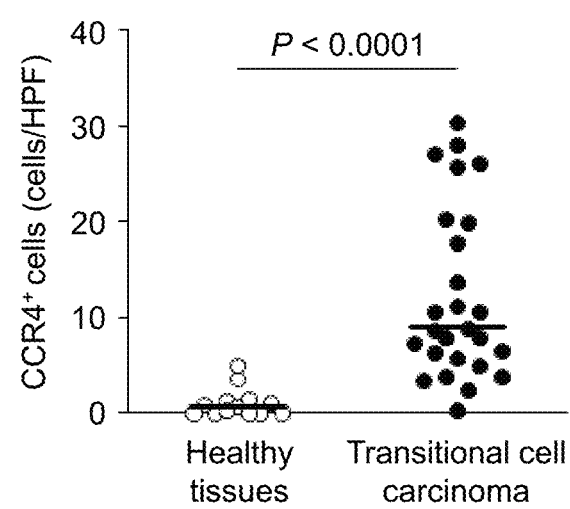
FIG. 6 is a view showing the number of CCR4-positive cells infiltrating into tumor, per high power field, in transitional cell carcinoma.

Using canine bladder transitional cell carcinoma tissues, the expression of CCR4 as a receptor for CCL17 was analyzed according to immunohistochemistry. As a result, infiltration of CCR4-positive cells was observed in the transitional cell carcinoma. FIG. 5 shows an immunohistochemically stained image of transitional cell carcinoma, wherein the portions seen as black points in the black-and-white photograph are sites in which CCR4-positive cells are present. FIG. 6 shows the number of CCR4-positive cells per high power field (HPF) in transitional cell carcinoma. Since the CCR4-positive cells are monocytes having a narrow cytoplasm, these cells were morphologically considered to be lymphocytes. Furthermore, the number of infiltrating Tregs showed a strong positive correlation with the number of infiltrating CCR4-positive cells (r=0.8334, P<0.0001).

[Example 4] Confirmation of CCR4 Expression in Tumor-Infiltrating Tregs

Figure 7:
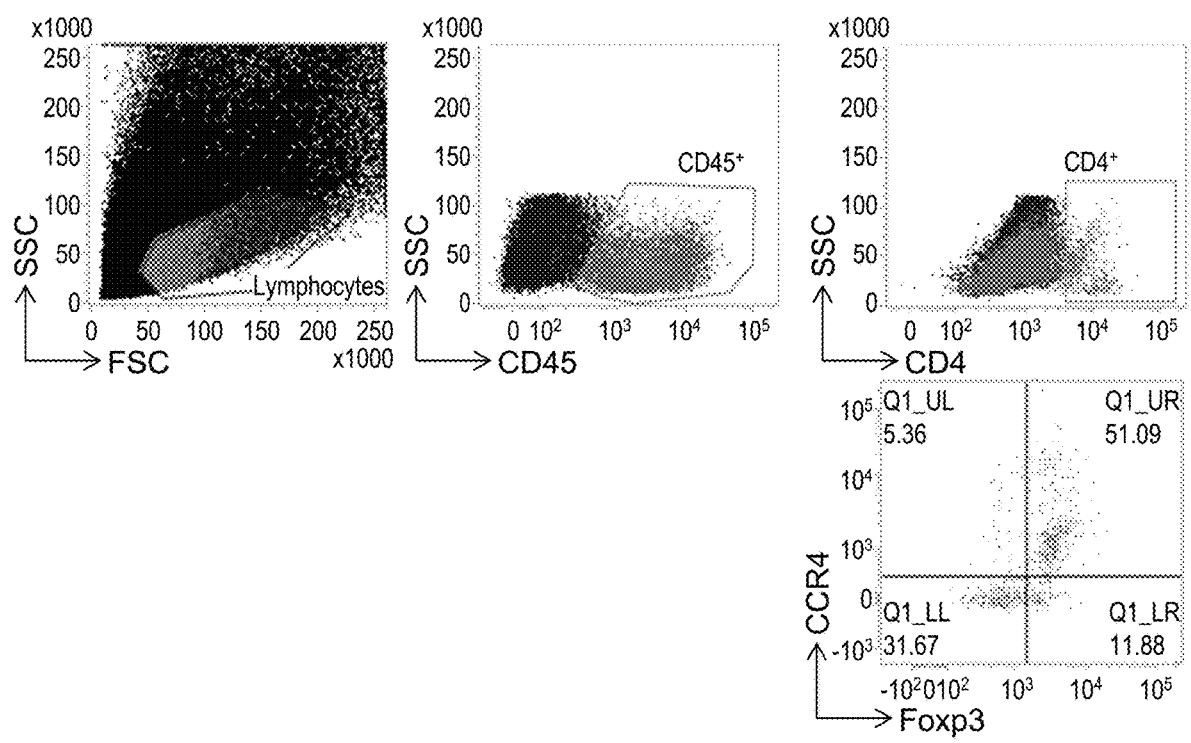
FIG. 7 is a view showing the expression of CCR4 in Tregs infiltrating into tumor.

Using surgically resected transitional cell carcinoma fresh tissues, flow cytometry (FACSVerse, BD Bioscience) was carried out. A lymphocyte fraction was selected from a cell population comprised in the tumor, based on a cell size (FSC) and cytoplasm fullness (SSC). Further, a cell population positive to CD45 as a leukocyte marker and a cell population positive to CD4 as a helper T cell marker were also selected. The expression of Foxp3 and CCR4 serving as Treg markers was confirmed in this helper T cell population. As a result, a majority of Foxp3-positive Tregs that have infiltrated into the tumor expressed CCR4 (FIG. 7).

As mentioned above, it was demonstrated that infiltration of Tregs into canine tumor tissues (in particular, transitional cell carcinoma) is associated with a CCL17-CCR4 pathway.

[Example 5] Studies Regarding Cross-Reactivity of Existing CCR4 Inhibitors with Canine CCR4

Figure 8:
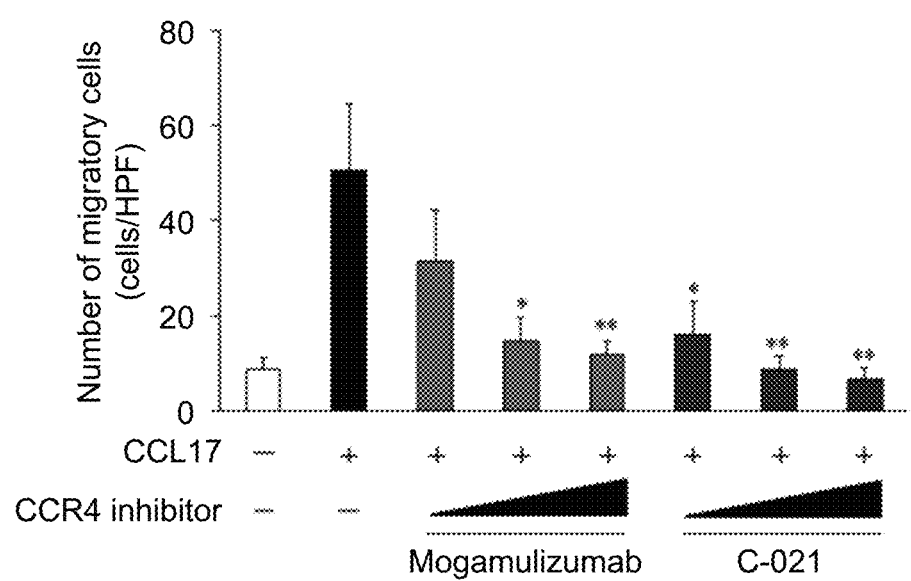
FIG. 8 is a view showing that Mogamulizumab and C-021 function as canine CCR4 inhibitors.

As inhibitors reacting against existing human CCR4, there are an anti-human CCR4 antibody (Mogamulizumab) (Kyowa Kirin Co., Ltd.) and a CCR4 antagonist (C-021; 2-[1,4'-bipiperidin]-1'-yl-N-cycloheptyl-6,7-dimethoxy-4-quinazolinamine dihydrochloride) (SANTA CRUZ BIOTECHNOLOGY). Thus, the cross-reactivity of these inhibitors with canine CCR4 was studied. Using a canine lymphocyte cell line (CL-1) expressing canine recombinant CCL17 and CCR4, a chemotaxis assay was carried out with a membrane chamber. As a result, migration of CL-1 by the recombinant CCL17 was significantly suppressed by addition of Mogamulizumab or C-021 (FIG. 8). From these results, it was found that these CCR4 inhibitors (a neutralizing antibody and a low-molecular-weight compound antagonist) also function in dogs.

[Example 6] Single Administration of Anti-Human CCR4 Antibody to Healthy Dog

Figure 9:
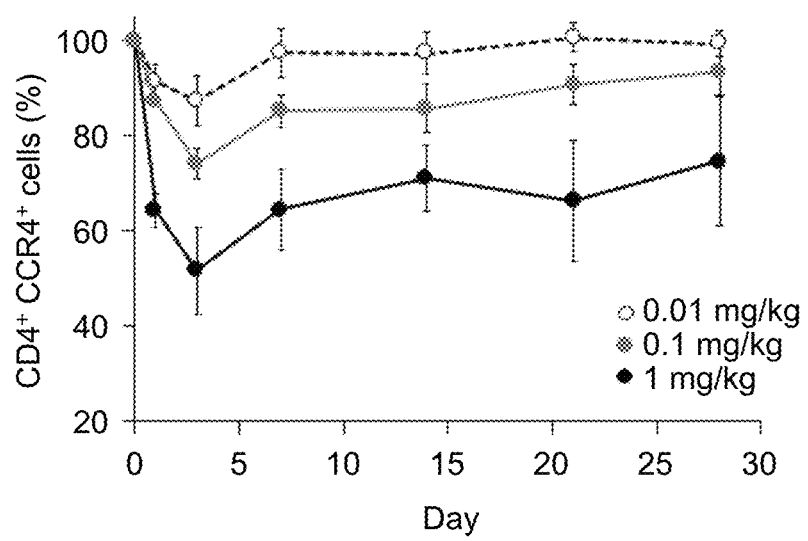
FIG. 9 is a view showing the influence of administration of an anti-human CCR4 antibody to healthy dogs.

In order to confirm the medicinal effects and safety of the anti-human CCR4 antibody (Mogamulizumab) in dogs, Mogamulizumab was intravenously administered to a healthy dog at a dose of 0.01 to 1 mg/kg, and the number of CCR4-positive T cells in blood was then evaluated according to flow cytometry. As a result, it was found that the number of CCR4-positive T cells in blood was reduced by half by administering Mogamulizumab to the dog at a dose of 1 mg/kg (FIG. 9). Furthermore, the effects were sustained for 3 to 4 weeks. When Mogamulizumab was administered at a dose of 0.01 to 0.1 mg/kg, no side effects were found. When Mogamulizumab was administered at a dose of 1 mg/kg, nausea, a slight increase in ALP, and a slight increase in CRP were observed. These side effects were improved 1 week after the administration, without any treatments. Hence, it was found that administration of Mogamulizumab to a dog at a dose of 1 mg/kg guarantees both efficacy and safety.

Figure 10:
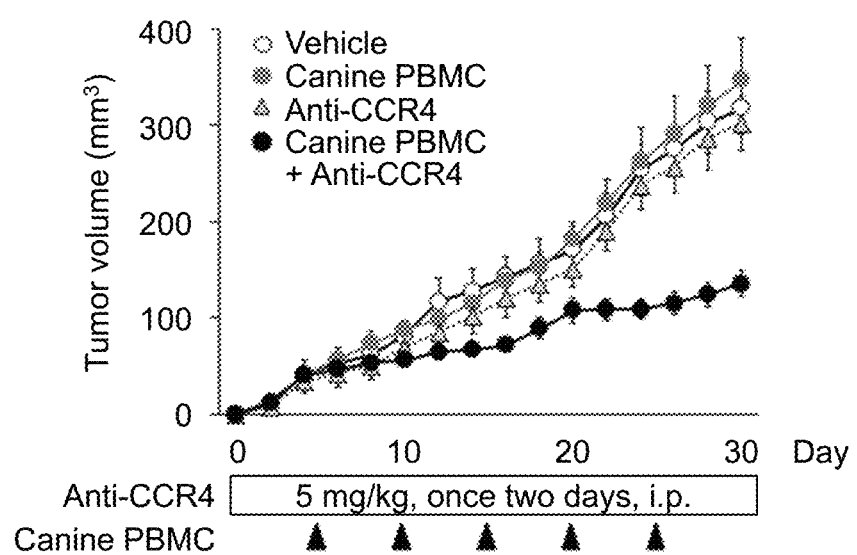
FIG. 10 is a view showing the antitumor effects of an anti-human CCR4 antibody on cancer-bearing mouse models.
Figure 11:
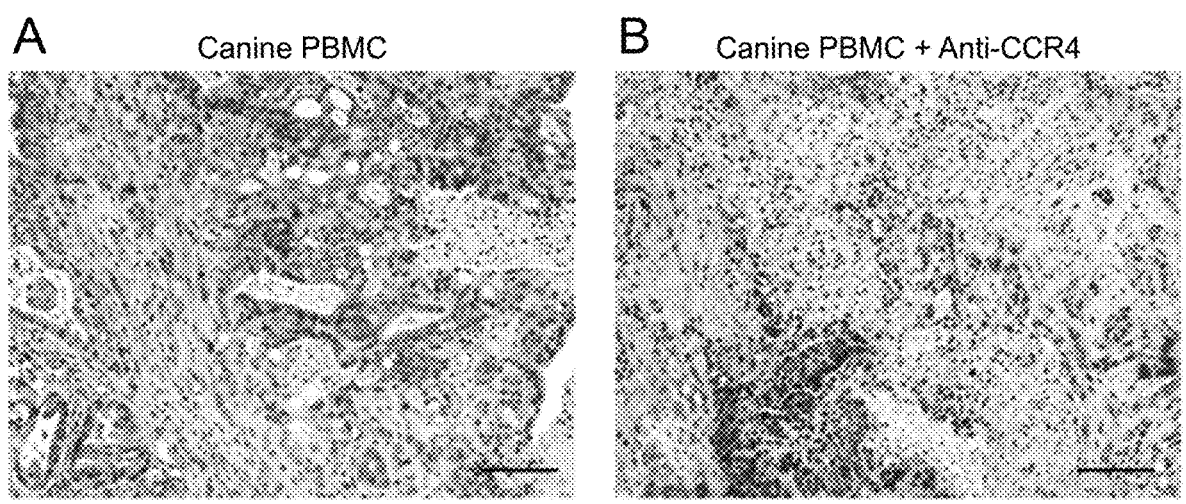
FIG. 11 is a view showing histopathologic examination images (H & E stained images) of tumor tissues upon administration of an anti-human CCR4 antibody to cancer-bearing mouse models.
Figure 12:
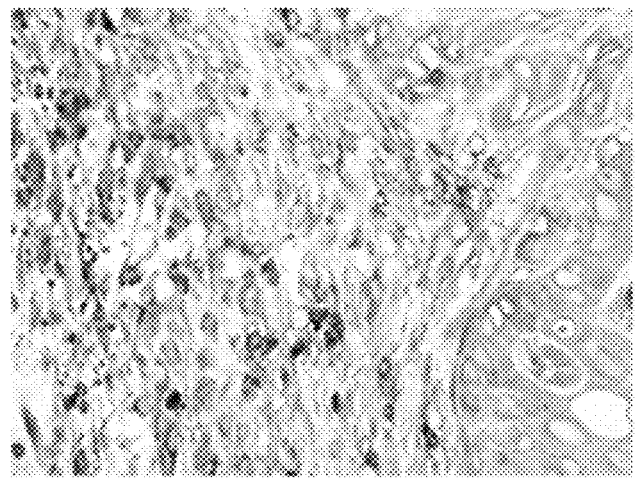
FIG. 12 is a view showing immunohistochemically stained images of Foxp3 in tumor tissues upon administration of canine PBMC, or canine PBMC and Mogamulizumab to cancer-bearing mouse models.
Figure 12:
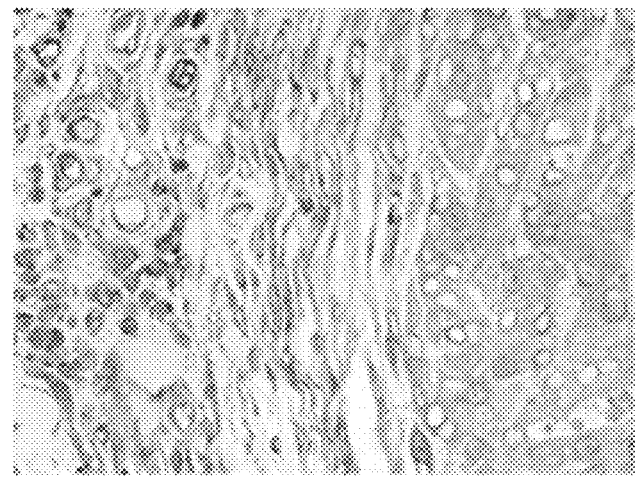
Figure 13:
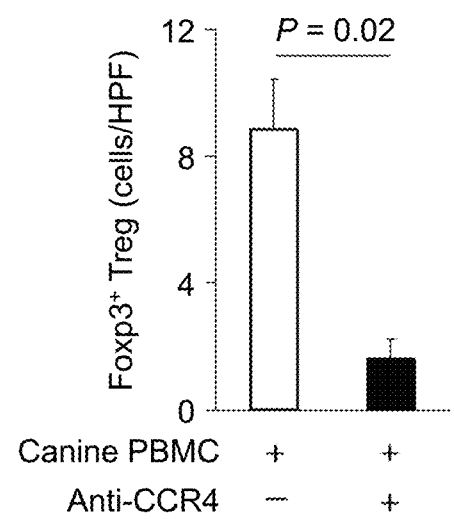
FIG. 13 is a view showing the number of Tregs infiltrating into tumor, per high power field, upon administration of canine PBMC, or canine PBMC and Mogamulizumab to cancer-bearing mouse models.

[Example 7] Studies Regarding Antitumor Effects of Anti-Human CCR4 Antibody, Using Cancer-Bearing Mouse Models In order to evaluate the antitumor effects of the anti-human CCR4 antibody (Mogamulizumab), cancer-bearing models were produced by transplanting a canine transitional cell carcinoma cell line into hyperimmune deficient mice (NOG mice; NOD/Shi-scid, IL-2RγKO, In-Vivo Science Inc.). These cancer-bearing mouse models were divided into four groups, namely, a solvent group (normal saline; Vehicle), a canine peripheral blood monocyte (PBMC) group comprising Tregs and cytotoxic T cells; a Mogamulizumab group (Anti-CCR4); and a combined use group of canine PBMC and Mogamulizumab. A comparison was made among the groups, in terms of the tumor volume of the transplanted transitional cell carcinoma cells. As a result, only in the combined use group of canine PBMC and Mogamulizumab, the growth of the tumor was significantly suppressed (FIG. 10). The tumor tissues were collected from each group at the end point, and the collected tumor tissues were subjected to a histopathologic examination involving H & E (Hematoxylin-Eosin) staining. The results are shown in FIG. 11. FIG. 11A shows the results of the canine PBMC group, whereas FIG. 11B shows the results of the combined use group of canine PBMC and Mogamulizumab. In FIG. 11, the whitish portion in the black-and-white photograph indicates a focus of necrosis. As shown in FIG. 11, in the combined use group of canine PBMC and Mogamulizumab, an expansion of the focus of necrosis was observed, in comparison to other groups. Furthermore, intratumoral infiltration of Tregs was evaluated by performing immunohistochemistry on Foxp3. FIG. 12 shows immunohistochemically stained images of Foxp3 in the canine PMBC group (FIG. 12A) and in the combined use group of canine PBMC and Mogamulizumab (FIG. 12B). FIG. 13 shows the number of Foxp3-positive Tregs per high power field (HPF) in the canine PMBC group and in the combined use group of canine PBMC and Mogamulizumab. In FIG. 12, the portions seen as black points in the black-and-white photograph are sites in which Foxp3-positive Tregs are present. As shown in FIG. 12 and FIG. 13, in the canine PBMC group, intratumoral infiltration of Tregs was observed, but in the combined use group of canine PBMC and Mogamulizumab, infiltration of Tregs was significantly suppressed.

From the aforementioned results, it became clear that, in cancer-bearing mouse models into which a canine tumor has been transplanted, inhibition of CCR4 suppresses intratumoral infiltration of Tregs and exhibits antitumor effects.

[Example 8] Clinical Tests Performed on Various Types of Canine Tumors

Figure 14:
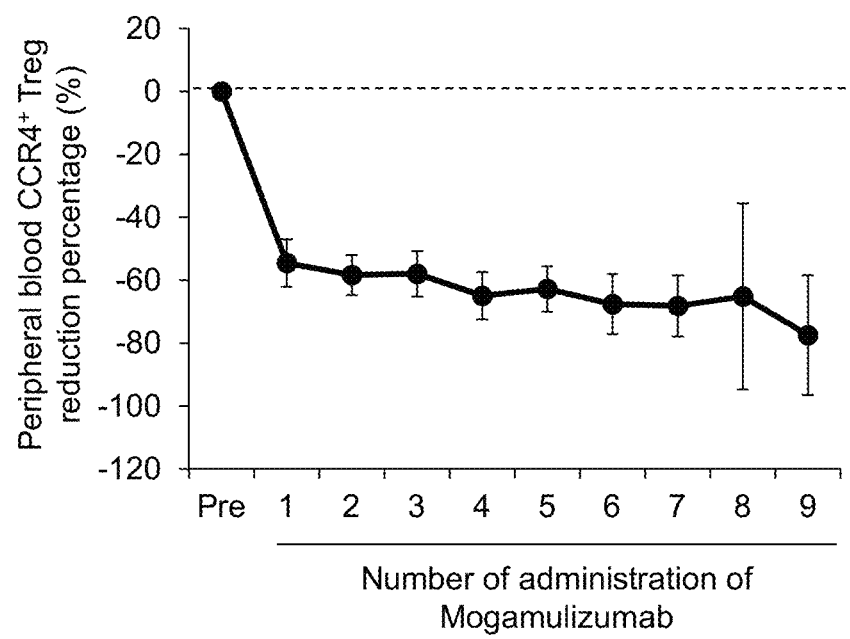
FIG. 14 is a view showing a change over time in CCR4-positive Tregs in peripheral blood, in the case of administering Mogamulizumab to dogs affected with tumor.
Figure 15:
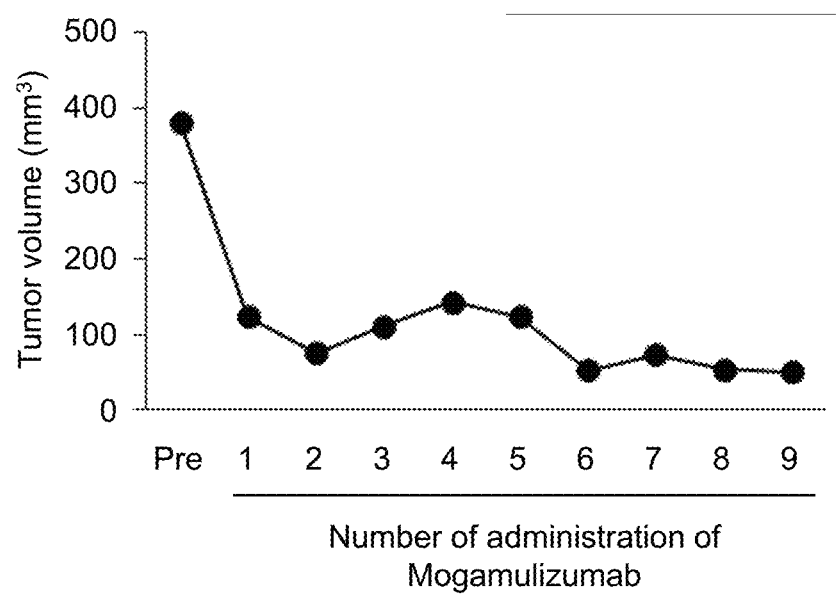
FIG. 15 is a view showing the antitumor effects of Mogamulizumab on transitional cell carcinoma.
Figure 16:
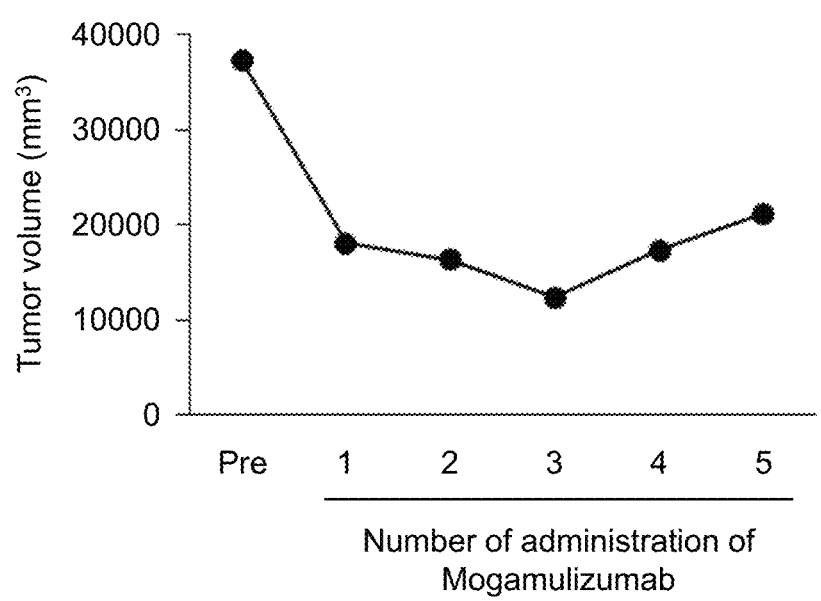
FIG. 16 is a view showing the antitumor effects of Mogamulizumab on prostate cancer.
Figure 17:
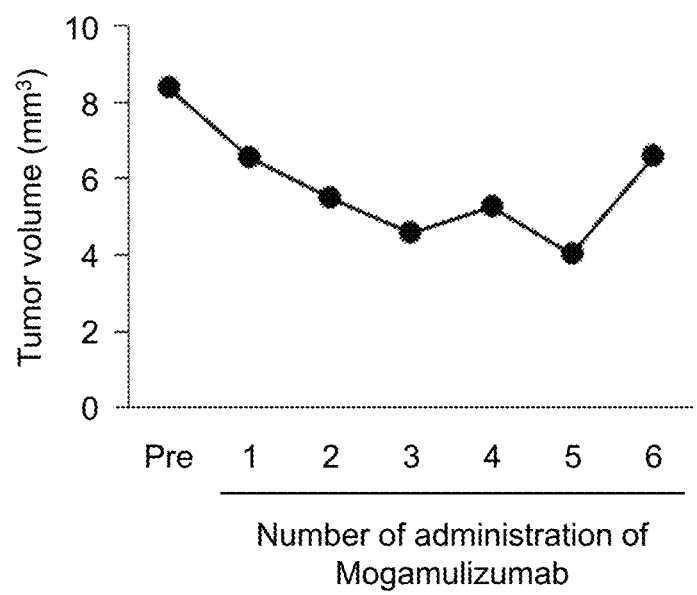
FIG. 17 is a view showing the antitumor effects of Mogamulizumab on breast cancer.

Using dogs affected with transitional cell carcinoma (11 cases), prostate cancer (4 cases), and breast cancer (2 cases), a clinical test regarding the anti-human CCR4 antibody (Mogamulizumab) was carried out. Mogamulizumab was intravenously administered at a dose of 1 mg/kg to dogs every three weeks, and thereafter, the number of CCR4-positive Tregs in the peripheral blood, a primary tumor volume, the presence or absence of the appearance of a metastatic lesion, and side effects were evaluated before and after the administration of Mogamulizumab. As a result, in all of the cases, after administration of Mogamulizumab, the number of CCR4-positive Tregs in peripheral blood was drastically reduced by the administration of Mogamulizumab. FIG. 14 shows the average CCR4-positive Treg reduction percentage of all of the cases. When the antitumor effects of Mogamulizumab were analyzed, in the case of transitional cell carcinoma, 5/11 cases (45.5%) had partial response, and 6/11 cases (54.5%) were stable (FIG. 15). In the case of prostate cancer, 2/4 cases (50%) had partial response, and 2/4 cases (50%) were stable (FIG. 16). In the case of breast cancer, 1/2 cases (50%) had partial response, and 1/2 cases (50%) was stable (FIG. 17). With regard to side effects caused by administration of Mogamulizumab, vomiting was observed in 3/17 cases (17.6%), a slight increase in ALP was observed in 3/17 cases (17.6%), and facial edema and/or redness were observed in 1/17 cases (5.9%). However, all of the side effects were mild.

From these results, it was demonstrated that the anti-CCR4 antibody (Mogamulizumab) would become a therapeutic agent effective for various types of canine tumors, having a few side effects.

In the present example, Tregs infiltrated into specific canine tumor tissues, and it became clear that infiltration of Tregs becomes a poor prognostic factor. It was demonstrated that a CCL17-CCR4 pathway is important for such intratumoral infiltration of Tregs. Moreover, it was found that inhibition of CCR4 causes a few side effects to dogs with transitional cell carcinoma, prostate cancer, and breast cancer, and thus that CCR4 inhibition becomes highly efficient therapeutic strategy. It is predicted that a CCR4 inhibitor will have therapeutic effects even on other tumors in which infiltration of Tregs has been observed (malignant melanoma, squamous cell carcinoma, and pulmonary adenocarcinoma).

[Example 9] Clinical Test of Mogamulizumab Canine Transitional Cell Carcinoma

Using dogs affected with transitional cell carcinoma (13 cases), a clinical test regarding the anti-human CCR4 antibody (Mogamulizumab) was carried out. A group to which Piroxicam alone was administered (single administration group of Piroxicam) was used as a control, and the effects of a group involving a combined use of Mogamulizumab and Piroxicam (combined use group with Mogamulizumab) were examined in comparison to the effects of the control. Thus, the effects of Mogamulizumab were evaluated. Piroxicam is a drug, which has been used in the chemotherapy of canine transitional cell carcinoma, and the effects of which have been recognized. Since the present example was a clinical test, from ethical point of view, the same treatment must have been performed on a test group (administration group of Mogamulizumab), as well as on the control group. Thus, Piroxicam was used in combination with Mogamulizumab. Mogamulizumab was intravenously administered to dogs at a dose of 1 mg/kg of body weight every three weeks (IV), whereas Piroxicam was orally administered to dogs at a daily dose of 0.3 mg/kg of body weight once a day (PO). To the control group, Piroxicam alone was administered (14 cases). The number of CCR4-positive Tregs in the peripheral blood and a tumor size were evaluated before and after the administration.

Figure 18:
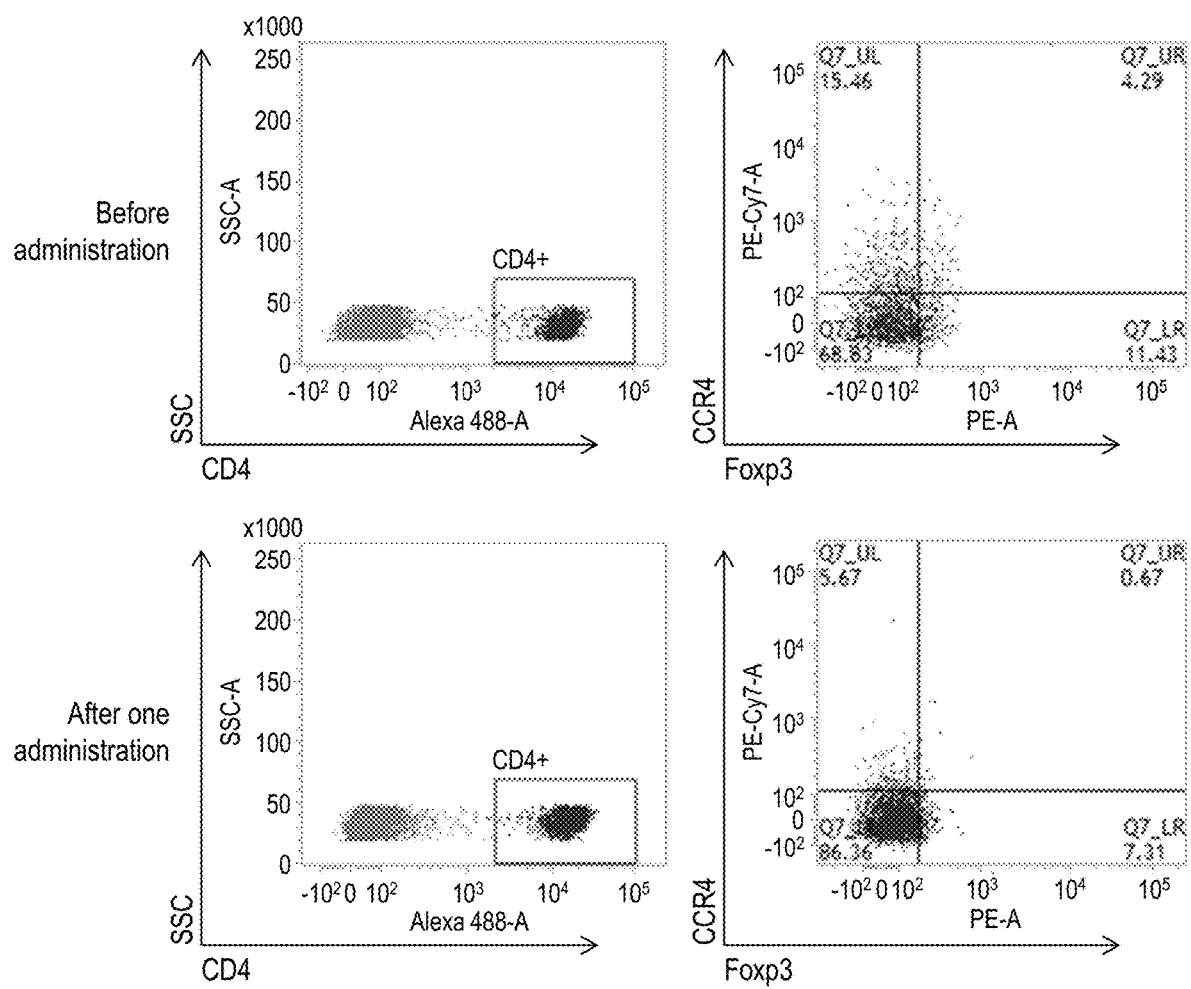
FIG. 18 is a view showing the measurement results of the number of CCR4-positive Tregs in the peripheral blood, using flow cytometry.
Figure 19:
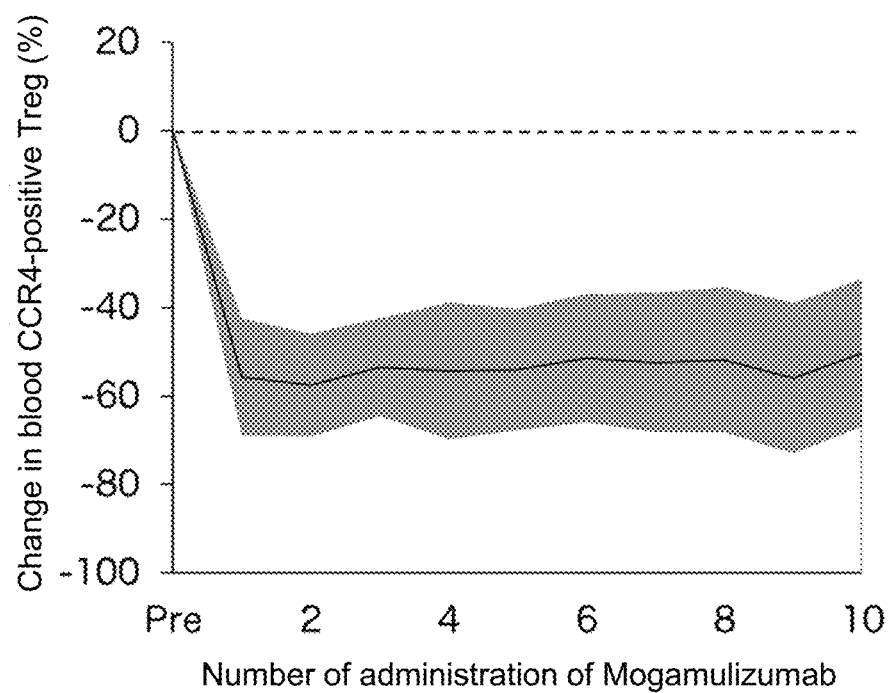
FIG. 19 is a view showing a change (%) in CCR4-positive Tregs in blood after administration of Mogamulizumab.

FIG. 18 shows the results obtained by measuring the number of CCR4-positive Tregs in the peripheral blood according to flow cytometry (FACSVerse, BD Bioscience), and FIG. 19 shows a change (%) in CCR4-positive Tregs in blood after administration of Mogamulizumab. The term "SSC" used in FIG. 18 indicates side scattered light, which is a light hit against a substance in a cell and is thereby scattered. SSC indicates the complexity of the internal structure of a cell, and reflects the normality of a nucleus or granule and the internal structure. As shown in FIGS. 18 and 19, the number of CCR4-positive Tregs in the peripheral blood was reduced after administration of Mogamulizumab.

Figure 20:
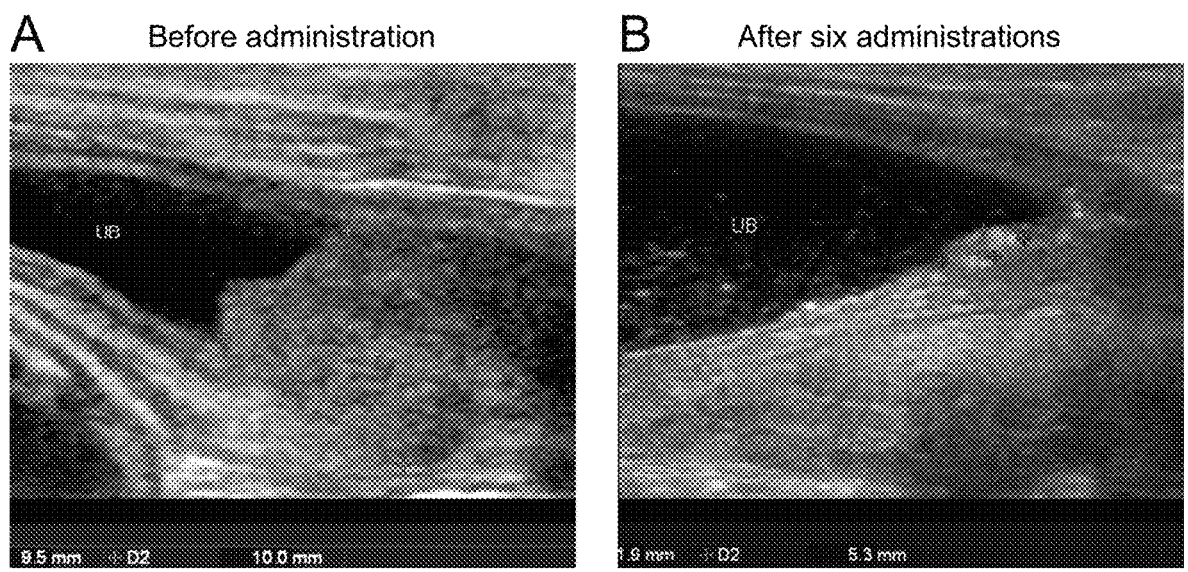
FIG. 20 is a view showing tumor sizes before and after administration of Mogamulizumab.
Figure 21:
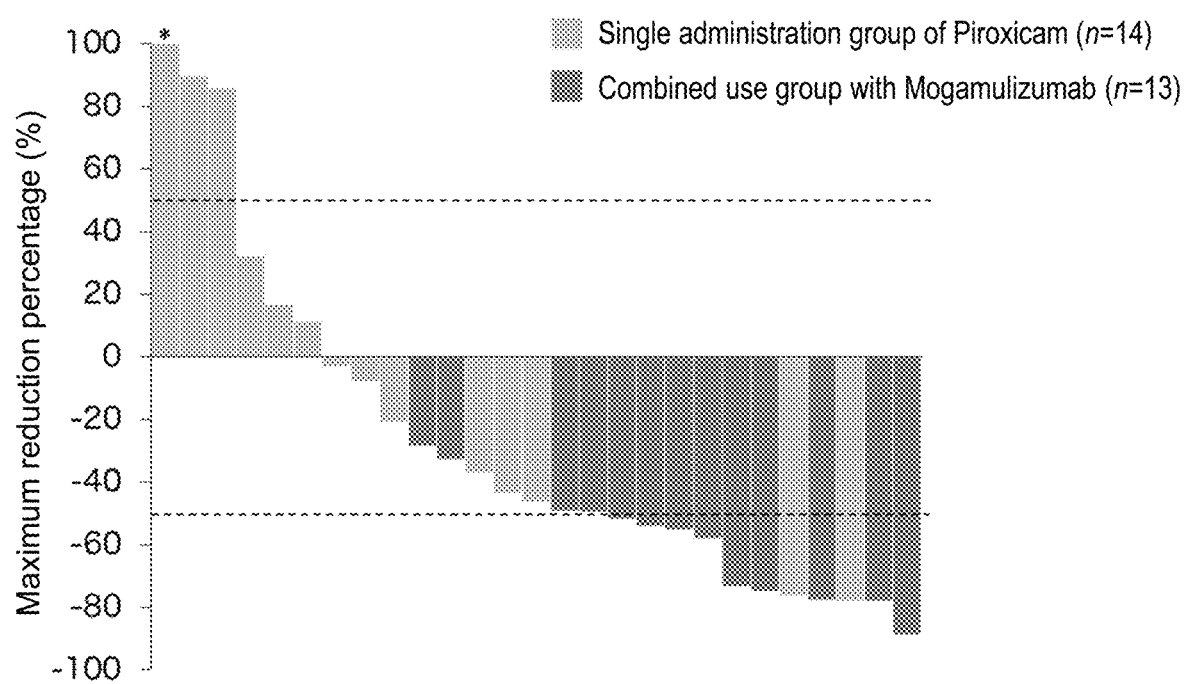
FIG. 21 is a view showing the maximum reduction percentages of the tumor volumes of a single administration group of Piroxicam and a combined use group with Mogamulizumab.

FIG. 20 shows tumor sizes before and after administration of Mogamulizumab. FIG. 20A shows the tumor size before administration of Mogamulizumab, whereas FIG. 20B shows the tumor size after administration of Mogamulizumab. FIG. 21 shows the maximum reduction percentages of the tumor volumes of a single administration group of Piroxicam and a combined use group with Mogamulizumab. FIG. 20 and FIG. 21 show that a tumor (mass) is reduced in the combined use group with Mogamulizumab, namely, that Mogamulizumab has the effect of reducing a tumor.

Figure 22:
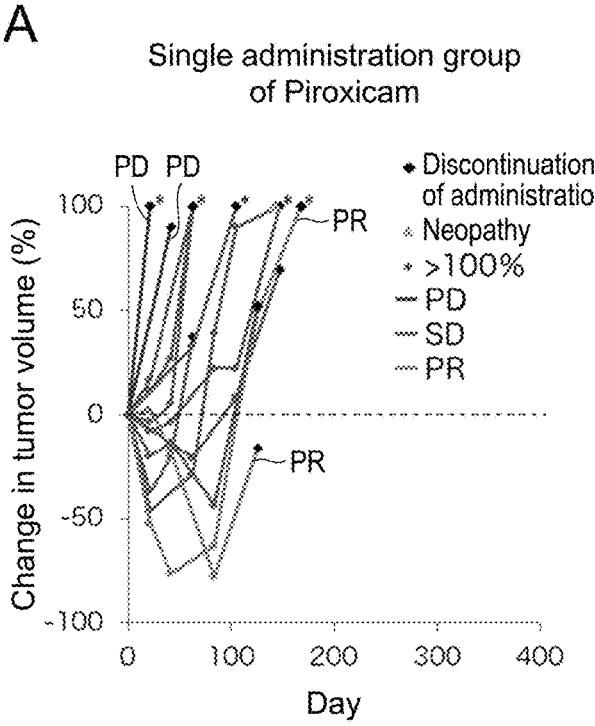
FIG. 22 is a view showing changes over time in the tumor volumes of a single administration group of Piroxicam and a combined use group with Mogamulizumab.
Figure 22:
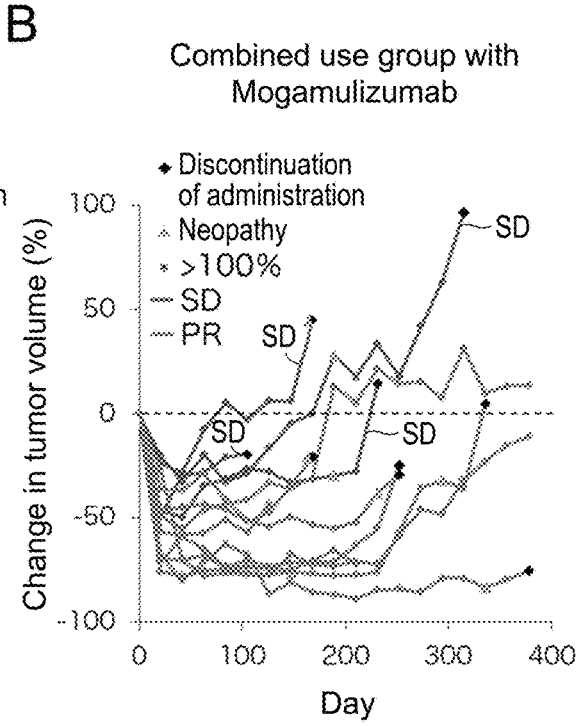

FIG. 22 shows changes over time in tumor volumes. FIG. 22A shows the results of the single administration group of Piroxicam, whereas FIG. 22B shows the results of the combined use group with Mogamulizumab. FIG. 23 shows the results obtained by comparing the therapeutic effects of a single administration group of Piroxicam with those of a combined use group with Mogamulizumab. In the figure, the terms "PR," "SD," and "PD" indicate definitions regarding a change in the size of a tumor in the midcourse of a treatment according to RECIST (Response Evaluation Criteria in Solid Tumors), which are evaluation criteria regarding therapeutic effects on solid cancers. Specifically, PR (Partial Response) indicates a state in which a sum of the sizes of tumors has been reduced by 30% or more, SD (Stable Disease) indicates a state in which the size of a tumor has not changed, and PD (Progressive Disease) indicates a state in which a sum of the sizes of tumors has been increased by 20% or more and the size has been increased by 5 mm or more as an absolute value, or a state in which a new lesion has appeared. RECIST is a common criterion that becomes an evaluation target according to an imaging diagnosis such as CT (Computed Tomography), wherein effects are judged based on a sum of "complete response (CR)" in which a tumor has completely disappeared and "stable disease (SD)" in which a tumor has been reduced by 30% or more. In the case of drug therapy, the "stable disease (SD)" state in which the size of a tumor has not changed is also considered to be the effects of a drug, and therapeutic effects are determined using a clinical efficacy percentage that is a sum of three conditions, namely, "complete response (CR)," "partial response (PR)," and "stable disease (SD)."

FIG. 22 and FIG. 23 show that a higher response percentage was obtained in the combined use group with Mogamulizumab than in the single administration group of Piroxicam, that is, Mogamulizumab exhibits significant therapeutic effects.

Figure 24:
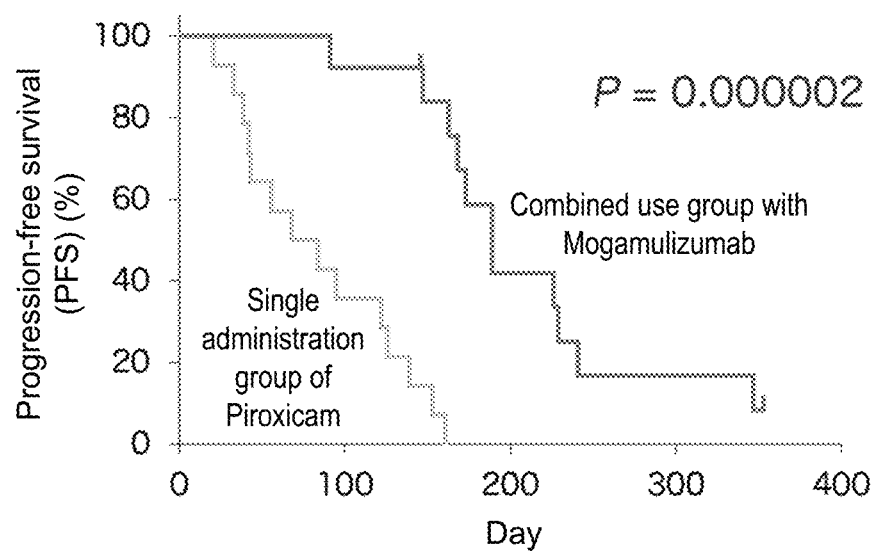
FIG. 24 is a view showing the overall survival periods (OS) of a single administration group of Piroxicam and a Mogamulizumab combined use group.
Figure 25:
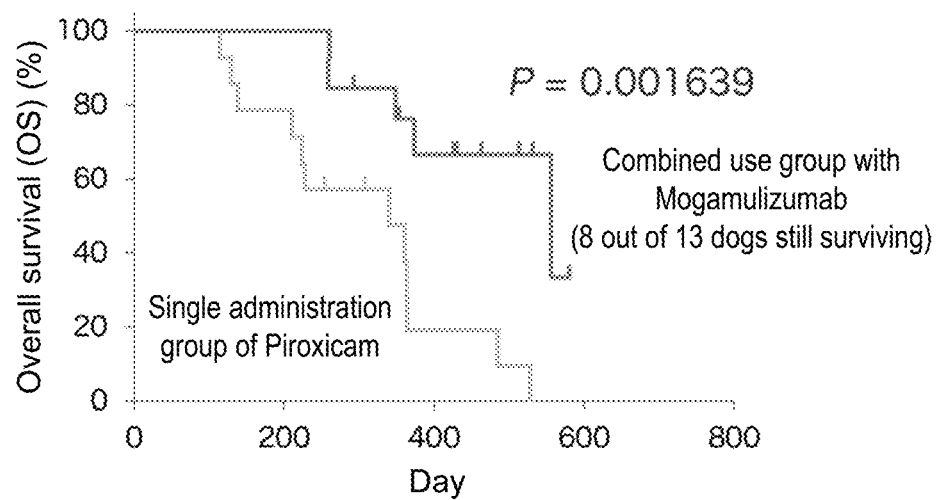
FIG. 25 is a view showing the overall survival periods (OS) of a single administration group of Piroxicam and a combined use group with Mogamulizumab.

FIG. 24 shows the progression-free survival periods (PFS) of a single administration group of Piroxicam and a combined use group with Mogamulizumab, and FIG. 25 shows the overall survival periods (OS) of a single administration group of Piroxicam and a combined use group with Mogamulizumab. In both types of survival periods, better improvement was observed in the combined use group with Mogamulizumab than in the single administration group of Piroxicam. These results show that Mogamulizumab exhibits significant therapeutic effects.

[Example 10] Determination of Effect of Treating Canine Tumor by Using Compound that Inhibits Binding of Canine CCL17 and Canine CCR4, in which CCL Level in Urine is Used as Indicator Urine was collected from the subject dogs used in clinical trial cases (combined use group with Mogamulizumab) before administration of the medicaments (Mogamulizumab and Piroxicam), and the CCL17 level in the urine was then measured. Moreover, the relationship between the tumor reduction percentage after administration of the medicaments and the CCL17 level in urine before administration thereof was examined.

The CCL17 (TARC) level was measured using Canine TARC ELISA Kit (CUSABIO (registered trademark)).

Figure 26:
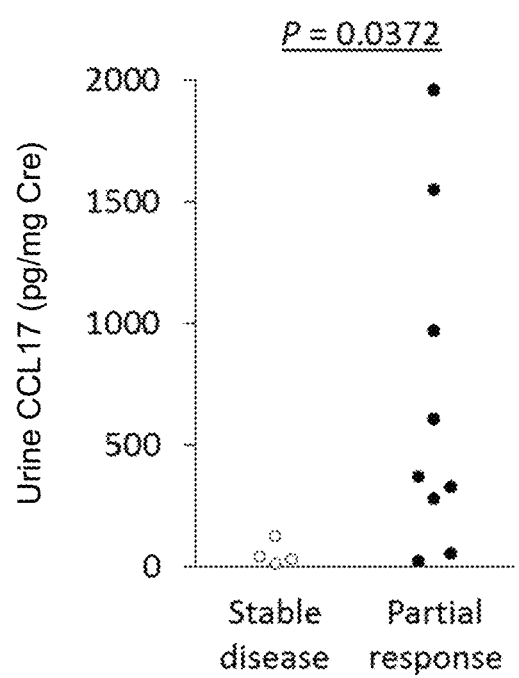
FIG. 26 is a view showing the relationship of a transitional cell carcinoma-affected dog that became SD (stable disease) as a result of administration of Mogamulizumab or a transitional cell carcinoma-affected dog that became PR (partial response) as a result of Mogamulizumab, with the CCL17 level in urine before administration of Mogamulizumab.

FIG. 26 shows the CCL17 level in the urine of subject dogs with SD (stable disease) (a state in which the size of a tumor has not changed) and PR (partial response) (a state in which a sum of tumor sizes has been reduced by 30% or more) before administration of the medicament. As shown in FIG. 26, as the CCL17 level in urine before administration of the medicament increased, it tended to become PR after administration thereof. That is to say, as the CCL17 level in urine increased, the therapeutic effects of Mogamulizumab also increased.

Figure 27:
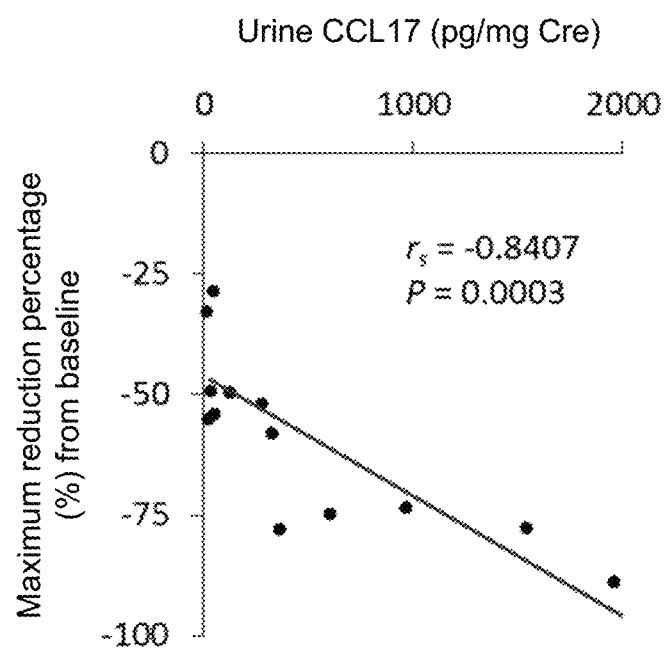
FIG. 27 is a view showing the relationship between the CCL level in the urine of a transitional cell carcinoma-affected dog before administration of Mogamulizumab with the tumor reduction percentage after administration thereof.

FIG. 27 shows the correlation between the CCL17 level in urine before administration of the medicament and the tumor reduction percentage after administration thereof. As shown in FIG. 27, as the CCL level in urine before administration of the medicament increased, the tumor reduction percentage after administration thereof tended to increase.

These results show that the CCL17 level in the urine of a subject dog can be used as an indicator for the therapeutic effects of Mogamulizumab on tumor.

INDUSTRIAL APPLICABILITY

A compound that inhibits the binding of CCL17 and CCR4, such as an anti-CCR4 antibody, can be used as an agent for treating canine tumor.

All publications, patents and patent applications cited in the present description are incorporated herein by reference in their entirety.

The invention claimed is:

1. A method for predicting the efficacy of a compound that inhibits the binding of canine CCL17 and canine CCR4 for the treatment of a canine tumor, using the level of CCL17 in a canine biological sample, wherein the compound is predicted to have high efficacy, when the CCL17 level in the biological sample is high, and administering the compound to the canine to treat the canine tumor, wherein the canine biological sample is urine.

2. The method according to claim 1, wherein the compound that inhibits the binding of canine CCL17 and canine CCR4 is an anti-CCR4 antibody.

3. The method according to claim 1, wherein the compound that inhibits the binding of canine CCL17 and canine CCR4 is 2-[1,4'-bipiperidin]-1'-yl-N-cycloheptyl-6,7-dimethoxy-4-quinazolinamine dihydrochloride.

4. The method according to claim 1, wherein the canine tumor is selected from the group consisting of transitional cell carcinoma, prostate cancer, breast cancer, malignant melanoma, squamous cell carcinoma, and pulmonary adenocarcinoma.

5. The method according to claim 4, wherein the canine tumor is selected from the group consisting of transitional cell carcinoma, prostate cancer, and breast cancer.

6. The method according to claim 1, wherein the CCL17 level is measured by an Enzyme-Linked ImmunoSorbent Assay (ELISA) using an anti-CCL17 antibody.

7. The method according to claim 6, wherein the anti-CCL17 antibody is Mogamulizumab.

* * * * *